United States Patent
Kasai et al.

(10) Patent No.: US 8,022,192 B2
(45) Date of Patent: Sep. 20, 2011

(54) PROCESS FOR PRODUCTION OF GLUCOPYRANOSYLOXYPYRAZOLE DERIVATIVE

(75) Inventors: Kiyoshi Kasai, Joetsu (JP); Tetsuji Ozawa, Joetsu (JP); Nobuhiko Fushimi, Azumino (JP); Hidetoshi Isawa, Joetsu (JP); Ken Kikuchi, Matsumoto (JP); Masahiro Kobayashi, Joetsu (JP); Junichi Sonehara, Joetsu (JP); Minoru Kubota, Joetsu (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 627 days.

(21) Appl. No.: 11/908,693

(22) PCT Filed: Mar. 16, 2006

(86) PCT No.: PCT/JP2006/305295
§ 371 (c)(1),
(2), (4) Date: Sep. 14, 2007

(87) PCT Pub. No.: WO2006/098413
PCT Pub. Date: Sep. 21, 2006

(65) Prior Publication Data
US 2009/0062518 A1   Mar. 5, 2009

(30) Foreign Application Priority Data
Mar. 17, 2005  (JP) ................. 2005-076644

(51) Int. Cl.
*C07H 17/02* (2006.01)
*A61K 31/7056* (2006.01)

(52) U.S. Cl. ........................ 536/17.4; 514/27

(58) Field of Classification Search ........................ None
See application file for complete search history.

(56) References Cited

U.S. PATENT DOCUMENTS

| | | | |
|---|---|---|---|
| 7,084,123 B2 * | 8/2006 | Fujikura et al. | 514/27 |
| 2003/0087843 A1 | 5/2003 | Washburn | |
| 2004/0006025 A1 | 1/2004 | Ohsumi et al. | |
| 2004/0063646 A1 | 4/2004 | Fujikura et al. | |
| 2004/0132669 A1 | 7/2004 | Nishimura et al. | |
| 2004/0147729 A1 | 7/2004 | Fujikura et al. | |
| 2004/0176308 A1 | 9/2004 | Shiohara et al. | |
| 2005/0143424 A1 * | 6/2005 | Maezono et al. | 514/340 |
| 2005/0233982 A1 | 10/2005 | Himmelsbach et al. | |

FOREIGN PATENT DOCUMENTS

| | | |
|---|---|---|
| JP | 2003-012686 A | 1/2003 |
| WO | WO 01/16147 A1 | 3/2001 |
| WO | WO 02/36602 AI | 5/2002 |
| WO | WO 02/053573 A1 | 7/2002 |
| WO | WO 02/068439 A1 | 9/2002 |
| WO | WO 02/098893 A1 | 12/2002 |
| WO | WO 03/020737 A1 | 3/2003 |
| WO | WO03/090783 * | 6/2003 |
| WO | WO 2005/021566 A2 | 3/2005 |

OTHER PUBLICATIONS

Greene and Wuts, "Protective Groups in Organic Synthesis" Published 1999 by John Wiley and Sons, pp. 17-23, 76-99, and 170-172.*

* cited by examiner

*Primary Examiner* — Eric S Olson
(74) *Attorney, Agent, or Firm* — Sughrue Mion, PLLC

(57) ABSTRACT

The present invention relates to a method for preparing the glucopyranosyloxypyrazole derivatives which are useful as agents for the prevention or treatment of a disease associated with hyperglycemia such as diabetes, diabetic complications, obesity or the like. A glucopyranosyloxypyrazole derivative can be easily and efficiently prepared by allowing a benzylpyrazole derivative represented by the general formula:

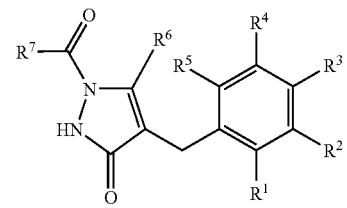

wherein $R^1$, $R^2$, $R^3$, $R^4$ and $R^5$ may be the same or different, for example each of them is a hydrogen atom, a halogen atom or an alkyl, alkoxy, arylmethyloxy group or the like, $R^6$ is an alkyl group, for example $R^7$ is a hydrogen atom or an alkyl, alkoxy, arylmethyloxy group or the like, to react with a compound represented by the general formula:

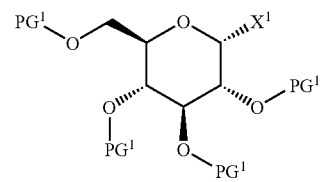

wherein as an example, $PG^1$ is a pivaloyl group or the like, as an example, $X^1$ is a bromine atom or the like, therefore the present invention is extremely useful as a method for preparing pharmaceutical compounds.

1 Claim, No Drawings

PROCESS FOR PRODUCTION OF GLUCOPYRANOSYLOXYPYRAZOLE DERIVATIVE

CROSS-REFERENCE TO RELATED APPLICATIONS

This application is a national stage application of PCT international application PCT/JP2006/305295, filed Mar. 16, 2006, which claims priority to foreign application JP2005-076644, filed Mar. 17, 2005 in Japan.

TECHNICAL FIELD

The present invention relates to a method for preparing glucopyranosyloxypyrazole derivatives useful as intermediates for manufacturing medicaments.

More particularly, the present invention relates to a method for preparing the glucopyranosyloxypyrazole derivatives which are useful as agents for the prevention or treatment of a disease associated with hyperglycemia such as diabetes, diabetic complications, obesity or the like. For example, the present invention relates to a method for preparing a glucopyranosyloxypyrazole derivative represented by the general formula:

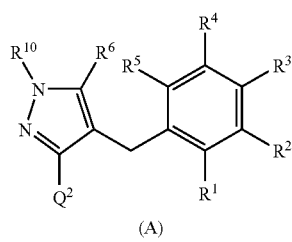

(A)

[Chem. 1]

wherein $R^1$, $R^2$, $R^3$, $R^4$ and $R^5$ may be the same or different, each of them is a hydrogen atom, a halogen atom, a $C_{1-6}$ alkyl group, a halo$C_{1-6}$ alkyl group, a $C_{3-6}$ cycloalkyl group, a $C_{3-6}$ cycloalkyloxy group, a $C_{3-6}$ cycloalkyl ($C_{1-6}$ alkoxy) group, a $C_{1-6}$ alkoxy group, a $C_{1-6}$ alkylthio group, a halo$C_{1-6}$ alkoxy group, an aryl group, an aryloxy group, a heteroaryl group, an aryl ($C_{1-6}$ alkyl) group, an aryl ($C_{1-6}$ alkoxy) group, a $C_{2-6}$ alkenyl group, a $C_{2-6}$ alkynyl group, a hetero$C_{3-6}$ cycloalkyl group, a hetero$C_{3-6}$ cycloalkyloxy group, a hetero$C_{3-6}$ cycloalkyl($C_{1-6}$ alkyl) group, a $C_{1-6}$ alkoxy group substituted by an amino group which is mono-substituted by a $C_{1-6}$ alkyl group or a $C_{1-6}$ alkoxy group substituted by an amino group which is di-substituted by a $C_{1-6}$ alkyl group, $R^6$ is a $C_{1-6}$ alkyl group, a halo$C_{1-6}$ alkyl group or a $C_{3-6}$ cycloalkyl group, $R^{10}$ is a hydrogen atom, a $C_{1-6}$ alkyl group, a $C_{3-6}$ cycloalkyl group, a $C_{3-6}$ cycloalkyl-substituted $C_{1-6}$ alkyl group, an aryl ($C_{1-6}$ alkyl) group, a hetero$C_{3-6}$ cycloalkyl group, a hetero$C_{3-6}$ cycloalkyl ($C_{1-6}$ alkyl) group or a group forming a prodrug, and $Q^2$ is a group represented by the general formula:

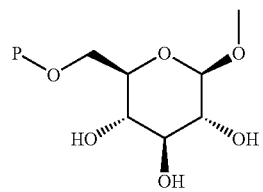

[Chem. 2]

in which P is a hydrogen atom or a group forming a prodrug. As the glucopyranosyloxypyrazole derivative, in addition, for example, Patent References 1 to 13 as described below can be illustrated.

BACKGROUND ART

It has been reported that the glucopyranosyloxypyrazole derivatives represented by the above general formula (A) are useful as agents for the prevention or treatment of a disease associated with hyperglycemia such as diabetes, diabetic complications, obesity or the like (for example, see Patent References 1 to 13).

Previously, as the method for preparing the glucopyranosyloxypyrazole derivatives represented by the above general formula (A), glycosylation using a benzylpyrazole derivative represented by the general formula:

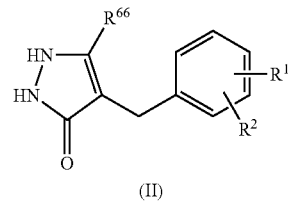

(II)

[Chem. 3]

wherein $R^{66}$ is a $C_{1-6}$ alkyl group, and $R^1$ and $R^2$ have the same meanings as defined above, and a hydroxy-protected α-D-glucopyranosylhalogen derivative in the presence of silver carbonate or silver oxide containing silver that is a heavy metal has been reported (for example, see Patent References 1 to 6).

However, when the glycosylation is carried out for a hydroxy-protected α-D-glucopyranosylbromide using the pyrazole derivative represented by the above general formula (II) wherein $R^{66}$ is a lower alkyl group under reported condition, side reactions that the pyrazole derivative represented by the above general formula (II) used in the reaction reacts with each other or that a nitrogen atom on the pyrazole ring is glycosylated occur, and the problems could not be avoided. And a problem that a special purification process to remove those by-products was needed existed. Furthermore, conditions to use a strong base or a reagent that contains silver that is the heavy metal was examined to suppress the side reaction. However, when the heavy metal is used for the manufacturing process of a medicine, a special purification process is necessary so that the heavy metal used does not remain in the medicine, and various analyze characteristics to be inspected to confirm whether the heavy metal remains in the medicine have to be conducted, therefore, there was a problem that a number of complex working increased. Heretofore, it is reported that reaction time becomes long if silver is not used, and for example, it requires several days to glycosylate, though other glycosylations without the use of the reagent that contains silver are examined to solve these problems (see Patent Reference 6). On the other hand, though a method by adding a phase-transfer catalyst to shorten the time of the glycosylation is also examined, so this time, various problems such as a problem that large excess of a sugar donor is needed, a problem that reactive yield is not constant, and a problem that conduct on an industrial scale is difficult are caused.

On the other hand, in Patent Reference 14, a method for obtaining a 5-thio-D-glucopyranoside derivative represented by the general formula:

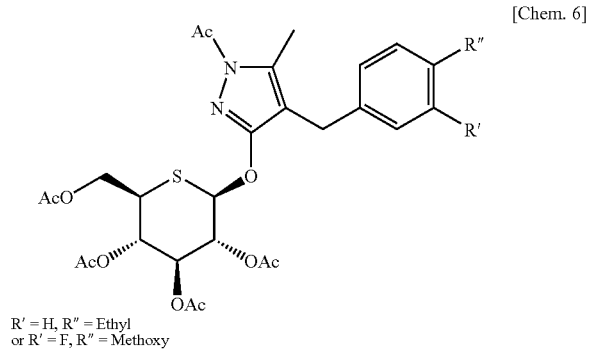

[Chem. 6]

R' = H, R" = Ethyl
or R' = F, R" = Methoxy by subjecting a pyrazole derivative represented by the general formula:

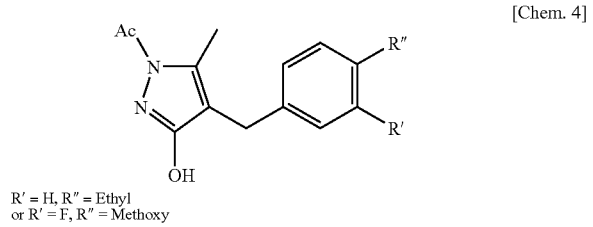

[Chem. 4]

R' = H, R" = Ethyl
or R' = F, R" = Methoxy and 2,3,4,6-tetra-O-acetyl-5-thio-D-glucose represented by a formula:

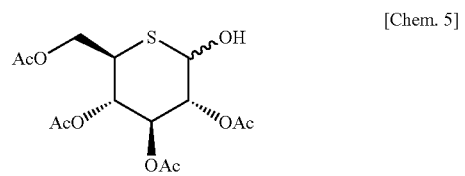

[Chem. 5]

to Mitsunobu reaction that uses triphenylphosphine and diisopropylazodicarboxylate is described. However, this reaction is different from the present invention because it is a different product (a 5-thio-D-glucopyranoside derivative) by a different method for preparing (Mitsunobu reaction) by the use of a different substrate 2,3,4,6-tetra-O-acetyl-5-thio-D-glucose. Moreover, in the above Patent Reference 14, it is not described that this reaction is applicable to manufacturing of an α-D-glucopyranosylhalogen derivative. And because the α/β selectivity of the product is not excellent, Mitsunobu reaction described in the above Patent Reference 14 has a problem that another process to remove the product of unnecessary configuration is needed, and unnecessary product should be disposed in economical respect. And Mitsunobu reaction has a problem of generating triphenylphosphine oxide difficult to remove as a by-product.

As mentioned above, the methods ever reported are not always satisfactory, and the development of a easier and more efficient process of manufacturing has been desired.

Patent Reference 1: International Publication WO02/053573 pamphlet;
Patent Reference 2: International Publication WO01/16147 pamphlet;
Patent Reference 3: International Publication WO02/068439 pamphlet;
Patent Reference 4: International Publication WO02/36602 pamphlet;
Patent Reference 5: International Publication WO02/020737 pamphlet;
Patent Reference 6: International Publication WO02/088157 pamphlet;
Patent Reference 7: Japanese Patent Publication 2003-012686;
Patent Reference 8: International Publication WO2005/021566 pamphlet;
Patent Reference 9: Japanese Patent Publication 2004-137245;
Patent Reference 10: International Publication WO02/098893 pamphlet;
Patent Reference 11: International Publication WO2004/014932 pamphlet;
Patent Reference 12: International Publication WO2004/018491 pamphlet;
Patent Reference 13: International Publication WO2004/019958 pamphlet;
Patent Reference 14: International Publication WO2004/089967 pamphlet.

DISCLOSURE OF THE INVENTION

Problem to be Solved by the Invention

The object of the present invention is to provide a method for preparing the glucopyranosyloxypyrazole derivatives which are useful as agents for the prevention or treatment of a disease associated with hyperglycemia such as diabetes, diabetic complications, obesity or the like. More particularly, it is to provide a novel method for preparing the glucopyranosyl-oxypyrazole derivative represented by the above general formula (A) or a pharmaceutically acceptable salt thereof.

Means of Solving the Problems

As a result that the present inventors have studied earnestly to solve the above problem, it was found that the glucopyranosyloxypyrazole derivative represented by the above general formula (A) or a pharmaceutically acceptable salt thereof is able to be prepared easily by allowing a benzylpyrazole derivative represented by the general formula:

[Chem. 7]

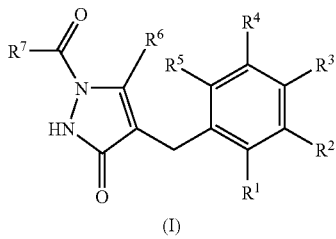

(I)

wherein $R^1$, $R^2$, $R^3$, $R^4$ and $R^5$ may be the same or different, each of them is a hydrogen atom, a halogen atom, a $C_{1-6}$ alkyl group, a halo$C_{1-6}$alkyl group, a $C_{3-6}$cycloalkyl group, a $C_{3-6}$cycloalkyloxy group, a $C_{3-6}$ cycloalkyl ($C_{1-6}$ alkoxy) group, a $C_{1-6}$ alkoxy group, a $C_{1-6}$ alkylthio group, a halo$C_{1-6}$ alkoxy group, an aryl group, an aryloxy group, a heteroaryl group, an aryl ($C_{1-6}$ alkyl) group, an aryl ($C_{1-6}$ alkoxy) group, a $C_{2-6}$ alkenyl group, a $C_{2-6}$ alkynyl group, a hetero$C_{3-6}$ cycloalkyl group, a hetero$C_{3-6}$ cycloalkyloxy group, a hetero$C_{3-6}$ cycloalkyl($C_{1-6}$ alkyl) group, a $C_{1-6}$ alkoxy group substituted by an amino group which is mono-substituted by a $C_{1-6}$ alkyl group or a $C_{1-6}$ alkoxy group substituted by an amino group which is di-substituted by a $C_{1-6}$ alkyl group, $R^6$ is a $C_{1-6}$ alkyl group, a halo$C_{1-6}$ alkyl group or a $C_{3-6}$ cycloalkyl group, and $R^7$ is a hydrogen atom, a $C_{1-6}$ alkyl group, a $C_{1-6}$ alkoxy group or an arylmethyloxy group, to react with an α-D-glucopyranosylhalogen derivative represented by the general formula:

[Chem. 8]

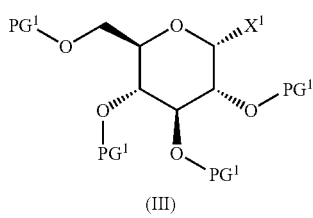

(III)

wherein $PG^1$ is an acetyl group, a pivaloyl group, an arylcarbonyl group or an arylmethyl group, and $X^1$ is a bromine atom or a chlorine atom, thereby forming the bases of the present invention.

That is, the present invention relates to a method and the like for preparing a glucopyranosyloxypyrazole derivative represented by the general formula:

[Chem. 11]

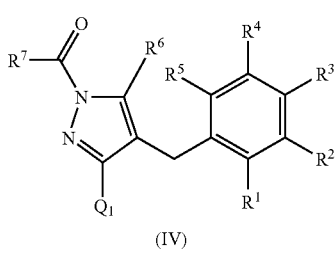

(IV)

wherein $Q^1$ is a group represented by the general formula:

[Chem. 12]

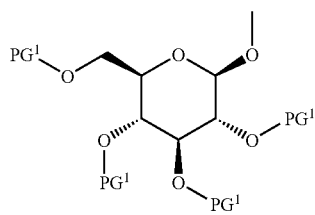

in which $PG^1$ has the same meaning as defined above, $R^1$, $R^2$, $R^3$, $R^4$, $R^5$, $R^6$ and $R^7$ have the same meanings as defined above comprising allowing a benzylpyrazole derivative represented by the general formula:

[Chem. 9]

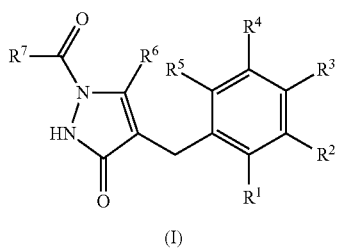

(I)

wherein $R^1$, $R^2$, $R^3$, $R^4$, $R^5$, $R^6$ and $R^7$ have the same meanings as defined above to react with an α-D-glucopyranosylhalogen derivative represented by the general formula:

[Chem. 10]

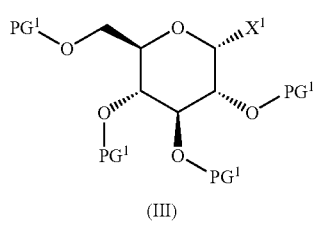

(III)

wherein $PG^1$ is an acetyl group, a pivaloyl group, an arylcarbonyl group or an arylmethyl group, and $X^1$ is a bromine atom or chlorine atom.

In the present invention, the following terms have the following meanings if not otherwise specified especially.

The term "halogen atom" means a fluorine atom, a chlorine atom, a bromine atom or an iodine atom.

The term "$C_{1-6}$ alkyl group" means a straight-chained or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, a 2-methylbutyl group, a hexyl group or the like.

The term "halo$C_{1-6}$ alkyl group" means the above $C_{1-6}$ alkyl group substituted by the same or different halogen atom as defined above. For example, a trifluoromethyl group, a 1,1,1-trifluoroethyl group, a 1,1,2,2-pentafluoroethyl group or the like can be illustrated.

The term "$C_{3-6}$ cycloalkyl group" means a cyclic alkyl group such as a cyclopropyl group, a cyclobutyl group, a cyclopentyl group, a cyclohexyl group or the like.

The term "$C_{1-6}$ alkoxy group" means a straight-chained or branched alkoxy group having 1 to 6 carbon atoms such as a methoxy group, an ethoxy group, a propoxy group, an isopropoxy group, a butoxy group, an isobutoxy group, a sec-butoxy group, a pentyloxy group, an isopentyloxy group, a neopentyloxy group, a tert-butoxy group, a tert-pentyloxy group, a 1-methylbutoxy group, a 2-methylbutoxy group, a hexyloxy group or the like.

The term "halo$C_{1-6}$ alkoxy group" means the above $C_{1-6}$ alkoxy group substituted by the same or different halogen atom as defined above. For example, a trifluoromethoxy group, a 1,1,1-trifluoroethoxy group, a 1,1,2,2-pentafluoroethoxy group or the like can be illustrated.

The term "$C_{1-6}$ alkylthio group" means a straight-chained or branched alkylthio group having 1 to 6 carbon atoms such as a methylthio group, an ethylthio group, a propylthio group, an isopropylthio group, a butylthio group, an isobutylthio group, a sec-butylthio group, a tert-butylthio group, a pentylthio group, an isopentylthio group, a neopentylthio group, a tert-pentylthio group, a 1-methylbutylthio group, a 2-methylbutylthio group, a hexylthio group or the like.

The term "$C_{2-7}$ acyl group" means a straight-chained, branched or cyclic acyl group having 2 to 7 carbon atoms such as an acetyl group, a propionyl group, a butyryl group, an isobutyryl group, a pivaloyl group, a hexanoyl group, a cyclohexylcarbonyl group or the like.

The term "$C_{2-7}$ alkoxycarbonyl group" means a straight-chained, branched or cyclic alkoxycarbonyl group having 2 to 7 carbon atoms such as a methoxycarbonyl group, an ethoxycarbonyl group, an isopropyloxycarbonyl group, an isobutylcarbonyl group, an isobutyloxycarbonyl group, a cyclohexyloxycarbonyl group or the like.

The term "$C_{1-6}$ alkoxy ($C_{2-7}$ acyl) group" means the above $C_{2-7}$ acyl group substituted by the above $C_{1-6}$ alkoxy group.

The term "aryl group" means an aromatic hydrocarbon group having 1 to 3 rings such as a phenyl group, a naphthyl group or the like, unsubstituted or substituted by a group described below independently selected from a group consisting of a halogen atom, a nitro group, a $C_{1-6}$ alkyl group, a halo$C_{1-6}$ alkyl group and a $C_{1-6}$ alkoxy group.

The term "arylcarbonyl group" means a carbonyl group substituted by the above aryl group, such as a benzoyl group or the like.

The term "aryl ($C_{1-6}$ alkyl) group" means a $C_{1-6}$ alkyl group substituted by the above aryl group. For example, a benzyl group, a 4-methoxybenzyl group, a 4-methylbenzyl group, a 4-nitrobenzyl group, a 4-chlorobenzyl group, a phenylethyl group or the like can be illustrated.

The term "arylmethyl group" means a methyl group substituted by the above aryl group among the above aryl ($C_{1-6}$ alkyl) group, such as a benzyl group, a 4-methoxybenzyl group, a 4-methylbenzyl group, a 4-nitrobenzyl group, a 4-chlorobenzyl group or the like.

The term "arylmethyloxy group" means a group substituted by the above arylmethyl group which is represented by arylmethyl-O—. For example, a benzyloxy group, a 4-methoxybenzyloxy group, a 4-methylbenzyloxy group, a 4-nitrobenzyloxy group, a 4-chlorobenzyloxy group or the like can be illustrated.

The term "aryl($C_{1-6}$ alkoxy) group" means a $C_{1-6}$ alkoxy group substituted by the above aryl group, and for example, a group represented by aryl-$CH_2$—O—, aryl-$(CH_2)_2$—O—, aryl-$(CH_2)_3$—O— or the like. A benzyloxy group, a 4-methoxybenzyloxy group, a 4-methylbenzyloxy group, a 4-nitrobenzyloxy group, a 4-chlorobenzyloxy group or the like can be illustrated.

The term "$C_{1-6}$ alkylsulfonyloxy group" means a sulfonyloxy group substituted by the above $C_{1-6}$ alkyl group such as a methanesulfonyloxy group, an ethanesulfonyloxy group or the like.

The term "arylsulfonyloxy group" means a group represented by aryl-$SO_2$—O— which is substituted by the above aryl group, for example, such as a benzensulfonyloxy group, a 4-methylbenzensulfonyloxy group, a 4-nitrobenzensulfonyloxy or the like.

The term "$C_{1-6}$ acyloxy group" means a group represented by ($C_{1-6}$ acyl)-O—, which substituted by the above $C_{1-6}$ acyl group.

The term "aryloxy group" means a group represented by aryl-O—, which is substituted by the above aryl group.

The term "mono($C_{1-6}$ alkyl)amino $C_{1-6}$ alkyl group" means the above $C_{1-6}$ alkyl group substituted by an amino group which is mono-substituted by the above $C_{1-6}$ alkyl group.

The term "di($C_{1-6}$ alkyl)amino $C_{1-6}$ alkyl group" means the above $C_{1-6}$ alkyl group substituted by an amino group which is di-substituted by the same or different above $C_{1-6}$ alkyl group.

The term "$C_{3-6}$ cycloalkyloxy group" means a group represented by ($C_{3-6}$ cycloalkyl)-O—, which is substituted by the above $C_{3-6}$ cycloalkyl group.

The term "$C_{3-6}$ cycloalkyl ($C_{1-6}$ alkoxy) group" means a $C_{1-6}$ alkoxy group substituted by the above $C_{3-6}$ cycloalkyl group.

The term "hetero$C_{3-6}$cycloalkyl group" means a cyclic alkyl group having 3 to 6 carbon atoms which contains any 1 to 4 hetero atoms selected from a group consisting of an oxygen atom, a sulfur atom and a nitrogen atom in the ring other than the binding position. For example, a tetrahydrofuran-3-yl group, a tetrahydropyran-3-yl group, a tetrahydropyran-4-yl group or the like can be illustrated.

The term "hetero$C_{3-6}$cycloalkyloxy group" means a group represented by hetero$C_{3-6}$cycloalkyl-O— which is substituted by the above hetero$C_{3-6}$cycloalkyl group. For example, a tetrahydrofuran-3-yloxy group, a tetrahydropyran-3-yloxy group, a tetrahydropyran-4-yloxy group or the like can be illustrated.

The term "hetero$C_{3-6}$cycloalkyl ($C_{1-6}$ alkyl) group" means the above $C_{1-6}$ alkyl group substituted by the above hetero$C_{3-6}$ cycloalkyl group. For example, a tetrahydrofuran-3-ylmethyl group, a tetrahydropyran-3-ylmethyl group, a tetrahydropyran-4-ylmethyl group or the like can be illustrated.

The term "$C_{2-6}$alkenyl group" means a straight-chained or branched unsaturated hydrocarbon having 2 to 6 carbon atoms, which has at least one double bond, for example, a vinyl group, an allyl group or the like can be illustrated.

The term "$C_{2-6}$alkynyl group" means a straight-chained or branched unsaturated hydrocarbon having 2 to 6 carbon atoms, which has at least one triple bond. For example, an ethynyl group, a propargyl group, a 2-butyn-1-yl group or the like can be illustrated.

The term "heteroaryl group" means a 5 to 10-membered aromatic heterocyclic group containing any 1 to 4 hetero atoms selected from a group consisting of an oxygen atom, a sulfur atom and a nitrogen atom in the ring other than the binding position or an aromatic heterocyclic group consisting of a 6-membered ring fused with a 5 or 6-membered ring containing any 1 to 4 hetero atoms selected from a group consisting of an oxygen atom, a sulfur atom and a nitrogen atom in the ring other than the binding position. These aromatic heterocyclic groups are unsubstituted or substituted by a group independently selected from a group consisting of the following groups: a halogen atom, a nitro group, a $C_{1-6}$ alkyl group, a halo$C_{1-6}$ alkyl group and a $C_{1-6}$ alkoxy group.

As a group forming a prodrug, for example, a protective group introduced into a hydroxy group or a nitrogen atom which can usually be used in a prodrug, such as a $C_{2-7}$ acyl group, a $C_{2-7}$ alkoxycarbonyl group or a $C_{1-6}$ alkoxy($C_{2-7}$ acyl) group can be illustrated.

The present invention is explained in detail as follows. The present inventors found that as shown in the scheme 1 described below, a glycosylation with a hydroxy-protected α-D-gluco-pyranosylbromide can be conducted using the above general formula (I) as a manufacturing intermediate, without using the reagent containing silver that is the heavy metal which has been reported up to now. Moreover, unlike with the method using a benzylpyrazole derivative represented by the above general formula (II), a method for preparing the present invention is an excellent method that has improved the side reaction which a pyrazole derivative used in the reaction reacts with each other and a nitrogen atom on the pyrazole ring is glycosylated even if a hydroxy-protected α-D-glucopyranosylhalogen derivative is used. Moreover, by the method for manufacturing of the present invention a compound represented by the general formula (IV) can be stereoselectively prepared in extremely high α/β selectivity, and the generation of an unnecessary product can be suppressed. And thus, it is a very excellent method from respect of manufacturing cost.

Scheme 1

[Chem. 19]

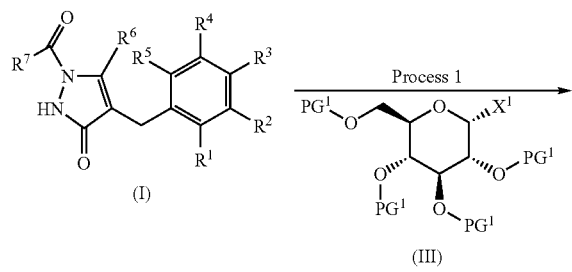

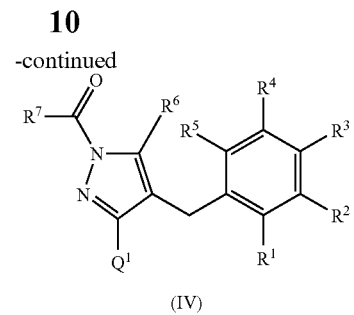

In the formula, $R^1$, $R^2$, $R^3$, $R^4$, $R^5$, $R^6$, $R^7$, $PG^1$, $Q^1$, and $X^1$ have the same meanings as defined above.

Process 1

The glycosylated compound represented by the above general formula (IV) can be prepared by allowing a benzylpyrazole derivative (I) to react with a sugar donor represented by the above general formula (III) in an inert solvent, in the presence of a base, usually at 20 to 60° C. As the base used in the reaction, a metal alkoxide such as potassium tert-butoxide or a reagent such as potassium carbonate, sodium carbonate, cesium carbonate or the like can be illustrated. As the solvent used in the reaction, for example, an ether solvent such as tetrahydrofuran, acetates, dimethylimidazolinone, N,N-dimethylformamide, N-methylpyrrolidone, N,N-dimethylacetamide, a ketone solvent such as acetone, acetonitrile, methylene chloride, 1,2-dichloroethane, or a mixture of solvents selected from the same or a mixture of the mixture and water can be illustrated. It is preferable to use 1 to 1.5 amounts of the sugar donor represented by the above general formula (III) used in the present reaction against the benzylpyrazole derivative (I). The reaction time is usually from 1 to 16 hours, varying based on a used starting material, solvent and reaction temperature.

Among the obtained compound (IV) in the above scheme 1, a glucopyranosyloxypyrazole derivative represented by the general formula (Aa) or (Ab) which is useful as an agent for the prevention or treatment of diabetes can be prepared by a method described in scheme 2 as follows with a compound represented by the above formula (IVa)

Scheme 2

[Chem. 20]

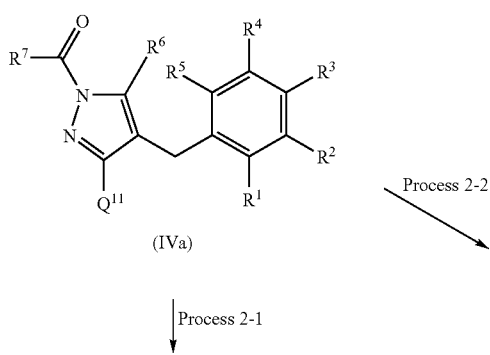

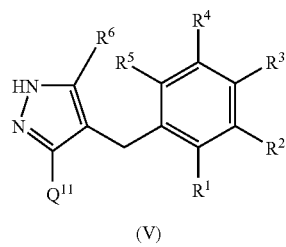

(V)

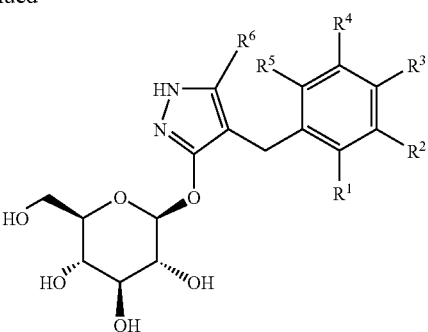

(Aa)

Process 2-4
R⁸—X²
(VI)

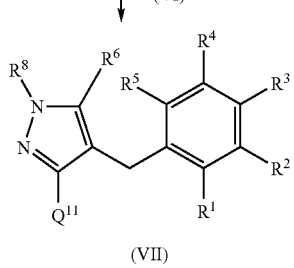

(VII)

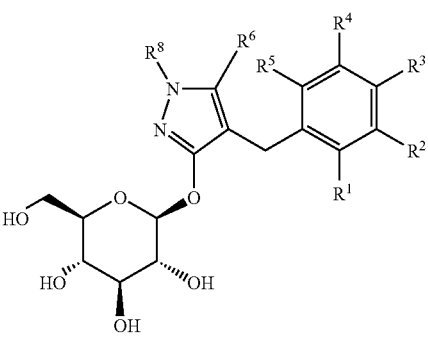

(Ab)

In the formula, $R^8$ is a $C_{1-6}$ alkyl group, a $C_{3-6}$ cycloalkyl group, a $C_{3-6}$ cycloalkyl($C_{1-6}$ alkyl) group, an aryl($C_{1-6}$ alkyl) group, a heteroC$_{3-6}$ cycloalkyl group or a heteroC$_{3-6}$ cycloalkyl ($C_{1-6}$ alkyl) group, $R^1$, $R^2$, $R^3$, $R^4$, $R^5$, $R^6$, $R^7$, $R^8$, $X^2$ and $Q^{11}$ have the same meanings as defined above.

Process 2-1

The glucopyranosyloxypyrazole derivative represented by the above general formula (V) can be prepared by leaving $R^7$CO— on a pyrazole ring, which is achieved to allow compound (IVa) to react in the presence of a base such as potassium hydrogen carbonate, potassium carbonate, sodium hydrogen carbonate, sodium carbonate or the like, in a solvent, usually at 20 to 80° C. As the solvent used in leaving of $R^7$CO— on a pyrazole ring, an alcohol solvent such as methanol, ethanol or the like, an ether solvent such as tetrahydrofuran, acetonitrile, dimethylimidazolinone, N,N-dimethylformamide, N-methylpyrrolidone, N,N-dimethylacetamide, acetone, methylethylketone, water, or a mixture of solvents selected from the same can be illustrated. As for amounts of the base used, it is preferable to use 0.1 to 1 amounts against the compound represented by the above general formula (IVa). The reaction time is usually from 2 to 24 hours, varying based on a used starting material, solvent and reaction temperature.

Process 2-2

About the compound (IVa), in case that $R^7$ is an arylmethyloxy group and $PG^{11}$ in $Q^{11}$ is an arylmethyl group, the glucopyranosyloxypyrazole derivative represented by the above general formula (Aa) can be prepared by subjecting the compound (IVa) to catalytic reduction in an alcohol solvent such as methanol, ethanol or the like, acetates, tetrahydrofuran or a mixture of solvents selected from the same, in the presence of metallic catalysts such as palladium, under a hydrogen atmosphere, usually at 20 to 60° C. The reaction time is usually from 2 to 24 hours, varying based on a used starting material, solvent, catalyst and reaction temperature.

Process 2-3

(1) Among a compound represented by the above general formula (V), in case that the protective group $PG^{11}$ is a benzyl group, debenzylation can be conducted in the ordinary method. For example, a glucopyranosyloxypyrazole derivative represented by the above general formula (Aa) can be prepared by subjecting the derivative to deprotection by catalytic reduction in an alcohol solvent such as methanol, ethanol or the like, acetates, tetrahydrofuran or a mixture of solvents selected from the same, in the presence of metallic catalysts such as palladium on carbon, under a hydrogen atmosphere, usually at 20 to 60° C. The reaction time is usually from 2 to 24 hours, varying based on a used starting material, solvent, catalyst and reaction temperature.

(2) Among the glucopyranosyloxypyrazole derivative represented by the above general formula (V), in case that the protective group $PG^{11}$ is a benzoyl group or a pivaloyl group, the glucopyranosyloxypyrazole derivative represented by the above general formula (Aa) can be prepared by subjecting the derivative to deprotection by hydrolysis under a basic condition, or by solvolysis in an alcohol solvent using a metal alkoxide usually at 20 to 60° C. The reaction time is usually from 2 to 24 hours, varying based on a used starting material, solvent, reaction condition and kinds of a protective group.

Process 2-4

The glucopyranosyloxypyrazole derivative represented by the above general formula (VII) can be prepared by subjecting the compound (V) to N-alkylation using an alkylation reagent (VI) represented by the general formula $R^8$—$X^2$ in the presence of a base. It is preferable to use 2 to 4 amounts of the alkylation reagent against the compound represented by the above general formula (V) usually at 0 to 60° C., using a metal alkoxide such as potassium tert-butoxide or the like, sodium hydride, potassium carbonate, sodium carbonate, cesium carbonate, sodium amide or the like, as the base, in N,N-dimethylformamide, N-methylpyrrolidone, N,N-dimethylacetamide, or a mixture of solvents selected from the same. The reaction time is usually from 1 to 12 hours, varying based on a used starting material, solvent and reaction temperature. A catalytic amount of sodium iodide or potassium iodide can be optionally used in the present N-alkylation.

Process 2-5

(1) Among the compound represented by the above general formula (VII), in case that $PG^{11}$ is a benzyl group, debenzylation can be conducted in the ordinary method. For example, the glucopyranosyloxypyrazole derivative represented by the above general formula (Ab) can be prepared by subjecting PG to elimination by catalytic reduction in an alcohol solvent such as methanol, ethanol or the like, acetates, tetrahydrofuran or a mixture of solvents selected from the same, in the presence of metallic catalysts such as palladium on carbon, under a hydrogen atmosphere, usually at 25 to 60° C. The reaction time is usually from 2 to 24 hours, varying based on a used starting material, solvent, catalyst and reaction temperature.

(2) Among the glucopyranosyloxypyrazole derivative represented by the above general formula (VII), in case that $PG^{11}$ is a benzoyl group or a pivaloyl group, the glucopyranosyloxypyrazole derivative represented by the above general formula (Ab) can be prepared by subjecting $PG^{11}$ to elimination by hydrolysis under a basic condition, or by solvolysis in an alcohol solvent using a metal alkoxide usually at 20 to 60° C. The reaction time is usually from 2 to 24 hours, varying based on a used starting material, solvent, reaction condition and kinds of a protective group.

Among the obtained compound (IV) in the above scheme 1, the glucopyranosyloxypyrazole derivative represented by the above general formula (Aa) can be prepared by a method described in the following scheme 3 with a compound represented by the following formula (IVb) wherein $PG^{11}$ in $Q^1$ is an acetyl group.

In the formula, $Q^{12}$ is the general formula:

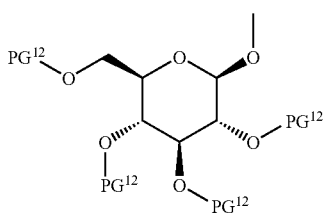

[Chem. 22]

wherein $PG^{12}$ is an acetyl group, $R^1$, $R^2$, $R^3$, $R^4$, $R^5$, $R^6$ and $R^7$ have the same meanings as defined above.

Process 3

The glucopyranosyloxypyrazole derivative represented by the above general formula (Aa) can be prepared by subjecting compound (IVb) to elimination of $R^7CO$— group on a pyrazole ring and $PG^{12}$ group at a sugar alcohol group at the same time, in the presence of a base such as a metal alkoxide such as sodium methoxide or the like, potassium carbonate, sodium carbonate, sodium hydroxide, potassium hydroxide, lithium hydroxide or the like, in an alcohol solvent such as methanol, ethanol or the like, acetonitrile, an ether solvent such as tetrahydrofuran, water or a mixture of solvents selected from the same at 20 to 80° C. As for amounts of the base used, it is preferable to use 0.2 to 7 amounts against the compound represented by the above general formula (IVb). The reaction time is usually from 2 to 12 hours, varying based on a used starting material, solvent and reaction temperature.

The obtained glucopyranosyloxypyrazole derivative represented by the general formula (Aa) or (Ab) in the above scheme 2 or 3 can be led to the compound represented by the above general formula (A), which has a prodrug forming group at $R^{10}$ or P, by prodrug-forming in the method described in the above Patent Reference 1 or the similar methods.

The 1-acyl-4-benzylpyrazole derivative represented by the above general formula (I) used as starting materials in the above-mentioned scheme 1 can be prepared in the method described in the following scheme 4, for example, using a benzylpyrazole derivative represented by the following general formula (VIII) which can be prepared in the method described in the above Patent References 1 to 6 or the similar methods.

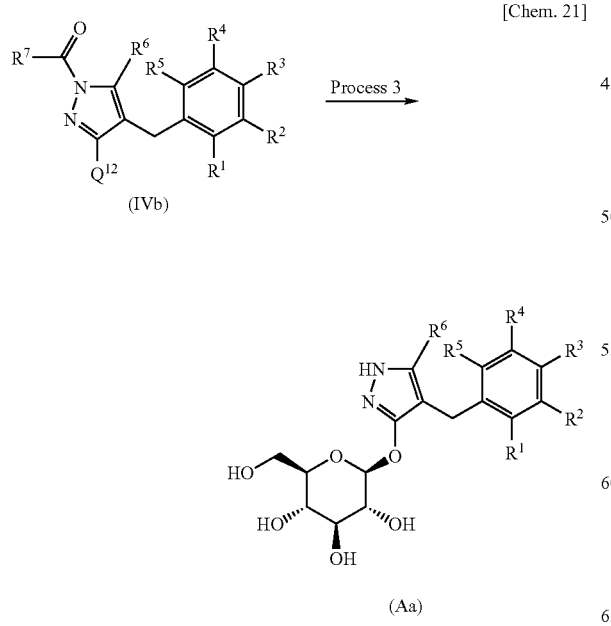

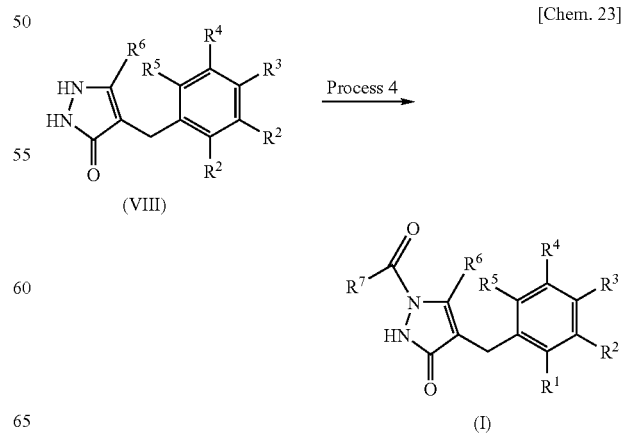

In the formula, $R^1$, $R^2$, $R^3$, $R^4$, $R^5$, $R^6$ and $R^7$ have the same meanings as defined above.

Process 4

By allowing a benzylpyrazol derivative (VIII) to react with $(R^7CO)_2O$, $R^7COO-COR^{77}$ wherein $R^{77}$ is a $C_{1-6}$ alkyl group, or a reactive functional derivative represented by the general formula $R^7 COX^3$ wherein $X^3$ is a halogen atom, a $C_{2-7}$ acyloxy group, an arylcarbonyloxy group, a $C_{1-6}$ alkylsulfonyloxy group, a group represented by a formula:

[Chem. 24]

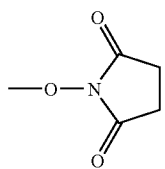

or an arylsulfonyloxy group which may have substitutents selected from a group consisting of a halogen atom, a nitro group and a $C_{1-6}$ alkyl group, in a solvent or without, usually at 0 to 100° C., the 1-acyl-4-benzylpyrazole derivative represented by the above general formula (I) of the present invention can be prepared. As the solvent used in the reaction, for example, N,N-dimethylformamide, acetonitrile, methylene chloride, 1,2-dichloroethane or a mixture of solvents selected from the same can be illustrated. As for used amounts of the acid anhydride or the reactive functional derivative used in the present reaction, it is preferable to use 1 to 3 amounts against the compound (VIII). The reaction time is usually from 1 to 12 hours, varying based on a used starting material, solvent and reaction temperature. The present reaction can be carried out without a base or an acid. In case that $R^6$ is not a bulky group such as methyl group, ethyl group and the like, it is more preferable to be carried out in the presence of a base or an acid. As a base, 1 to 2 amounts of pyridine, triethylamine, N,N-diisopropylethylamine, 1,8-diazabicyclo[5,4,0]-7-undecene, potassium hydrogen carbonate, potassium carbonate, sodium carbonate, sodium hydrogen carbonate, cesium carbonate or the like can be illustrated, as an acid, 0.1 to 1.5 amounts of acetic acid or p-tosic acid can be illustrated. On the other hand, in case that $R^6$ is a bulky group such as an isopropyl group, an isobutyl group, a sec-butyl group or the like, it is more preferable to be carried out under an acid condition, as an acid, 0.1 to 1.5 amounts of acetic acid or p-tosic acid can be illustrated.

These glucopyranosyloxypyrazole derivatives (A) can be converted into their pharmaceutically acceptable salts optionally in the usual way. Examples of these salts include acid addition salts with mineral acids such as hydrochloric acid, hydrobromic acid, hydroiodic acid, nitric acid, sulfuric acid, acetic acid, phosphoric acid and the like, acid addition salts with organic acids such as formic acid, acetic acid, adipic acid, citric acid, fumaric acid, maleic acid, oleic acid, lactic acid, stearic acid, succinic acid, tartaric acid, propionic acid, butyric acid, oxalic acid, malonic acid, malic acid, carbonic acid, glutamic acid, aspartic acid, methanesulfonic acid, benzenesulfonic acid, p-tolylsulfonic acid and the like, salts with organic amines such as 2-aminoethanol, piperidine, morpholine, pyrrolidine and the like, inorganic salts such as sodium salt, potassium salt, calcium salt, magnesium salt and the like can be illustrated.

The compound represented by the above general formula (III) used in the glycosylation as described in the above scheme 1 is commercially available or can be respectively prepared in the method described in "Journal of Chemical Society, pp. 636 to 649 (1959)" or the similar method when $PG^1$ is an acetyl group, a benzoyl group or a pivaloyl group and $X^1$ is a chlorine atom, in the method described in "Tetrahedron Letters, vol. 30, pp 3081-3084 (1989)" or the similar method when $PG^1$ is a benzyl group, or in the method described in "Liebigs Annalen der chemie, vol. 1, pp. 41 to 48 (1982)" or the similar method when $PG^1$ is a pivaloyl group and $X^1$ is a bromine atom. The other compound (III) can be prepared in the similar method as described above Among the 1-acyl-4-benzylpyrazole derivatives represented by the above general formula (I) of the present invention, there can be some tautomers (I') described in scheme as follows. The states change by the difference of the reaction condition. The 1-acyl-4-benzylpyrazole derivatives (I) of the present invention also include their tautomers (I').

Scheme 5

[Chem. 25]

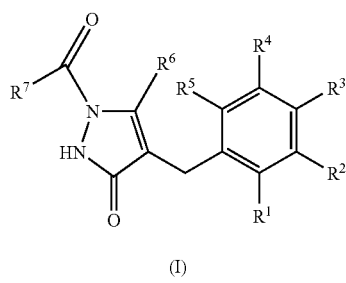

(I)

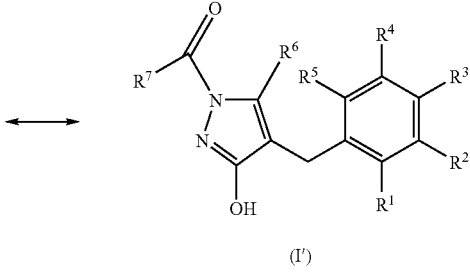

(I')

In the formula, $R^1$, $R^2$, $R^3$, $R^4$, $R^5$, $R^6$ and $R^7$ have the same meanings as defined above.

EFFECT OF THE INVENTION

According to a method for the preparation of the present invention, for example, the glucopyranosyloxypyrazole derivative represented by the above general formula (A) or a pharmaceutically acceptable salt thereof which is useful as an agent for the prevention or treatment of a disease associated with hyperglycemia such as diabetes, diabetic complications, obesity or the like can be prepared easily and efficiently. Moreover though α/β selectivity in the glycosylation is very excellent, it is a stereoselective method for preparing, and the glucopyranosyloxypyrazole derivative represented by the above general formula (A) or a pharmaceutically acceptable salt thereof can be prepared efficiently and effectively.

BEST MODE TO PRACTICE THE INVENTION

The present invention is further illustrated in more detail by way of the following Examples, however the invention is not limited thereto.

EXAMPLES

Reference Example 1

1-Acetyl-4-benzyl-1,2-dihydro-5-isopropyl-3H-pyrazol-3-one

4-Benzyl-1,2-dihydro-5-isopropyl-3H-pyrazol-3-one (1.50 g) was dissolved in tetrahydrofuran (6.0 g) at room temperature. Acetic anhydride (0.708 g) and acetic acid (0.0208 g) was added to the solution successively. After the reaction mixture was stirred at room temperature for 15 hours, the solvent was removed under reduced pressure. The residue was purified by column chromatography on silica gel (The product was eluted with dichloromethane at first, and then n-hexane/ethyl acetate=4/1) to give 1-acetyl-4-benzyl-1,2-dihydro-5-isopropyl-3H-pyrazol-3-one (1.38 g).

$^1$H-NMR (CDCl$_3$) δ (ppm) 1.13-1.19 (6H, m), 2.63-2.66 (3H, m), 2.75-2.80 (0.4H, m), 2.99-3.04 (0.6H, m), 3.63-3.69 (2H, m), 7.13-7.30 (5H, m), 8.26 (0.4H, br-s)

Reference Example 2

1-Acetyl-4-[(4-benzyloxy-2-methylphenyl)methyl]-1,2-dihydro-5-isopropyl-3H-pyrazol-3-one 1-Acetyl-4-[(4-benzyloxy-2-methylphenyl)methyl]-1,2-dihydro-5-isopropyl-3H-pyrazol-3-one was prepared in a similar manner described in (Reference Example 1) using 4-[(4-benzyloxy-2-methylphenyl)methyl]-1,2-dihydro-5-isopropyl-3H-pyrazol-3-one.

$^1$H-NMR (CDCl$_3$) δ (ppm): 1.1-1.2 (6H, m), 2.30 (1.2H, s), 2.32 (1.8H, s), 2.64 (1.2H, s), 2.65-2.8 (2.2H, m), 2.85-2.95 (0.6H, m), 3.53 (1.2H, s), 3.56 (0.8H, s), 5.02 (2H, s), 6.65-6.75 (1H, m), 6.75-6.85 (1H, m), 6.92 (0.4H, d, J=8.3 Hz), 6.98 (0.6H, d, J=8.3 Hz), 7.25-7.45 (5H, m), 8.12 (0.6H, s), 9.94 (0.4H, s)

Reference Example 3

4-Benzyl-1,2-dihydro-5-isopropyl-1-propionyl-3H-pyrazol-3-one

4-Benzyl-1,2-dihydro-5-isopropyl-3H-pyrazol-3-one (2.00 g) was dissolved in tetrahydrofuran (10 mL) at room temperature. Propionic anhydride (1.26 g) and propionic acid (0.012 g) was added to the solution successively. After the reaction mixture was stirred at room temperature for 3 hours, the solvent was removed under reduced pressure. The residue was purified by column chromatography on silica gel (eluent: dichloromethane/ethyl acetate=1/1) to give 4-benzyl-1,2-dihydro-5-isopropyl-1-propionyl-1H-pyrazol-3-one (1.98 g).

$^1$H-NMR (CDCl$_3$) δ (ppm): 1.11-1.32 (9H, m), 2.70-2.80 (0.4H, m), 2.91-3.16 (2.6H, m), 3.63-3.72 (2H, m) 7.14-7.28 (5H, m) 8.3 (0.4H, br-s)

Reference Example 4

1-Acetyl-4-benzyl-1,2-dihydro-5-methyl-3H-pyrazol-3-one

4-Benzyl-1,2-dihydro-5-methyl-3H-pyrazol-3-one (1.00 g) was suspended in N,N-dimethylformamide (5 mL) at room temperature. In addition, potassium carbonate (0.441 g) was added to the suspension, and the mixture was stirred for 30 minutes. Acetic anhydride (0.570 g) was added to the mixture in a dropwise manner at room temperature. The mixture was stirred at room temperature overnight and at 50° C. for 2 hours. In addition, the mixed solution of glacial acetic acid (0.191 g) and water (5.0 g) was added to the reaction mixture under stirring at room temperature. After confirming the precipitation of the crystals, water (25 g) was added to the mixture under stirring. The crystals were collected by filtration, washed with water and dried under reduced pressure to give a white solid of 1-acetyl-4-benzyl-1,2-dihydro-5-methyl-3H-pyrazol-3-one (0.92 g).

$^1$H-NMR (DMSO-d$_6$) δ (ppm): 2.41 (3H, s), 2.46 (3H, s), 3.61 (2H, s), 7.14-7.18 (3H, m), 7.24-7.28 (2H, m), 11.0 (1H, br)

Reference Example 5

1-Acetyl-1,2-dihydro-4-[(4-isopropoxyphenyl)methyl]-5-methyl-3H-pyrazol-3-one 1,2-Dihydro-4-[(4-isopropoxyphenyl)methyl]-5-methyl-3H-pyrazol-3-one (1.00 g) was suspended in N,N-dimethylformamide (5 mL) at room temperature. In addition, potassium carbonate (0.319 g) was added to the suspension, and the mixture was stirred for 30 minutes. Acetic anhydride (0.412 g) was added to the mixture in a dropwise manner at room temperature. The mixture was stirred at room temperature overnight and at 50° C. for 2 hours. In addition, the mixed solution of glacial acetic acid (0.139 g) and water (5.0 g) was added to the reaction mixture under stirring at room temperature. After confirming the precipitation of the crystals, water (25 g) was added to the mixture. The obtained crystals were collected by filtration, washed with water and dried under reduced pressure to give a white solid of 1-acetyl-1,2-dihydro-4-[(4-isopropoxy-phenyl)methyl]-5-methyl-3H-pyrazol-3-one (0.90 g).

$^1$H-NMR (DMSO-d$_6$) δ (ppm): 1.22 (6H, d, J=6.2 Hz), 2.40 (3H, s), 2.45 (3H, s), 3.52 (2H, s), 4.49-4.54 (1H, m), 6.78-6.81 (2H, m), 7.04-7.06 (2H, m), 11.0 (1H, br)

Reference Example 6

1-Acetyl-4-[(3-fluoro-4-methylphenyl)methyl]-1,2-dihydro-5-methyl-3H-pyrazol-3-one 4-[(3-Fluoro-4-methylphenyl)methyl]-1,2-dihydro-5-methyl-3H-pyrazol-3-one (1.00 g) was suspended in N,N-dimethyl-formamide (5 mL) at room temperature. Potassium carbonate (0.376 g) was added to the suspension, and the mixture was stirred for 30 minutes. Acetic anhydride (0.486 g) was added to the reaction mixture in a dropwise manner at room temperature. The mixture was stirred at room temperature overnight and at 50° C. for 2 hours. The mixture was cooled to room temperature under stirring, the mixed solution of glacial acetic acid (0.164 g) and water (5.0 g) was added to the mixture. After confirming the precipitation of the crystals, water (25 g) was added to the mixture. The obtained crystals were collected by filtration and washed with water. The obtained wet crystals were dried under reduced pressure to give a yellowish-white solid of 1-acetyl-4-[(3-fluoro-4-methylphenyl)methyl]-1,2-dihydro-5-methyl-3H-pyrazol-3-one (0.502 g).

$^1$H-NMR (DMSO-d$_6$) δ (ppm): 2.16 (3H, s), 2.40 (3H, s), 2.45 (3H, s), 3.58 (2H, s), 6.89-6.91 (2H, m), 7.14-7.17 (1H, m), 11.0 (1H, br-s)

Reference Example 7

1-Benzyloxycarbonyl-4-benzyl-1,2-dihydro-5-isopropyl-3H-pyrazol-3-one

4-Benzyl-1,2-dihydro-5-isopropyl-3H-pyrazol-3-one (2.00 g) was dissolved in N,N-dimethylformamide (5 mL) at room temperature. N-(Benzyloxycarbonyloxy)succinimide (2.42 g) was added to the solution. The mixture was heated to 50° C. and then stirred for 16 hours. After the addition of water (20 mL) and ethyl acetate (20 mL) to the reaction mixture, the aqueous layer was separated, and the organic layer was washed with water. The obtained organic layer was concentrated under reduced pressure, and the residue was purified by column chromatography on silica gel (eluent: ethyl acetate/dichloromethane=1/3 to 1/1) to give 1-benzyloxycarbonyl-4-benzyl-1,2-dihydro-5-isopropyl-3H-pyrazol-3-one (1.15 g).

$^1$H-NMR (DMSO-$d_6$) δ (ppm): 1.12 (6H, t, J=8.3 Hz), 1.80-2.10 (1H, m), 3.31 (2H, br-s), 3.39-3.70 (2H, m), 5.18 (0.4H, br-s), 5.37 (0.6H, br-s), 7.06-7.26 (5H, m), 7.36-7.49 (5H, m), 11.1 (0.6H, br-s), 12.3 (0.4H, br-s)

Reference Example 8

4-Benzyl-1-ethoxycarbonyl-1,2-dihydro-5-isopropyl-3H-pyrazol-3-one

N-Hydroxysuccinimide (1.06 g) was dissolved in tetrahydrofuran (10 g) at room temperature. Triethylamine (0.936 g) and ethyl chloroformate (1.00 g) were added to the solution successively. After stirring the reaction mixture at room temperature for 30 minutes, 4-benzyl-1,2-dihydro-5-isopropyl-3H-pyrazol-3-one (2.00 g) was added to the mixture at room temperature. After the reaction mixture was stirred at room temperature for 13 hours, the reaction mixture was stirred at 50° C. for 6 hours. The insoluble materials were removed, and the filtrate was concentrated under reduced pressure. The residue was purified by column chromatography on silica gel (eluent: n-hexane/ethyl acetate=4/1) to give 4-benzyl-1-ethoxycarbonyl-1,2-dihydro-5-isopropyl-3H-pyrazol-3-one.

$^1$H-NMR (CDCl$_3$) δ (ppm): 1.16-1.20 (6H, m), 1.39-1.49 (3H, m), 2.81-2.94 (1H, m), 3.71-3.72 (2H, m), 4.37-4.41 (0.9H, m), 4.52-4.57 (1.1H, m), 7.15-7.30 (5H, m), 9.38 (1H, br-s)

Reference Example 9

4-Benzyl-1,2-dihydro-1-formyl-5-isopropyl-3H-pyrazol-3-one

4-Benzyl-1,2-dihydro-5-isopropyl-3H-pyrazol-3-one (1.00 g) was dissolved in tetrahydrofuran (10 mL) at room temperature. A mixed anhydride of formic acid and acetic acid (0.489 g) and acetic acid (0.0140 g) were successively added to the solution. After stirring the reaction mixture at room temperature for 5 hours, the solvent was removed under reduced pressure. The residue was purified by column chromatography on silica gel (eluent: n-hexane:ethyl acetate=4:1) to give 4-benzyl-1,2-dihydro-1-formyl-5-isopropyl-3H-pyrazol-3-one (1.07 g).

$^1$H-NMR (CDCl$_3$) δ (ppm): 1.19 (6H, d, J=7.5 Hz), 3.00-3.06 (1H, m), 3.63 (2H, s), 7.14-7.30 (5H, m), 9.04 (1H, s)

Example 1

1-Acetyl-4-benzyl-5-isopropyl-3-(2,3,4,6-tetra-O-pivaloyl-β-D-glucopyranosyloxy)-1H-pyrazole To a solution of 1-acetyl-4-benzyl-1,2-dihydro-5-isopropyl-3H-pyrazol-3-one (1.26 g) in acetonitrile (20 mL) were added potassium carbonate (1.01 g) and 2,3,4,6-tetra-O-pivaloyl-β-D-glucopyranosyl bromide (2.96 g) under stirring at room temperature. In addition, the mixture was heated to 50° C. and stirred for 3 hours. After the completion of the reaction, the insoluble material was removed by filtration. The filtrate was concentrated under reduced pressure. The residue was purified by column chromatography on silica gel (eluent: n-hexane/ethyl acetate=10/1) to give 1-acetyl-4-benzyl-5-isopropyl-3-(2,3,4,6-tetra-O-pivaloyl-β-D-glucopyranosyloxy)-1H-pyrazole (2.68 g).

$^1$H-NMR (CDCl$_3$) δ (ppm): 1.03-1.05 (6H, m), 1.06 (9H, s), 1.12 (9H, s), 1.13 (9H, s), 1.19 (9H, s), 2.52-2.59 (4H, m), 3.65-3.76 (3H, m), 3.91-3.95 (1H, m), 4.09-4.12 (1H, m), 5.12 (1H, t, J=10 Hz), 5.27-5.30 (1H, m), 5.40 (1H, t, J=9.5 Hz), 5.46 (1H, d, J=8.0 Hz), 7.15-7.24 (5H, m)

Example 2

1-Acetyl-4-[(4-benzyloxy-2-methylphenyl)methyl]-5-isopropyl-3-(2,3,4,6-tetra-O-pivaloyl-β-D-glucopyranosyl-oxy)-1H-pyrazole 1-Acetyl-4-[(4-benzyloxy-2-methylphenyl)methyl]-5-isopropyl-3-(2,3,4,6-tetra-O-pivaloyl-β-D-glucopyranosyloxy)-1H-pyrazole was prepared in a similar manner described in (Example 1) using 1-acetyl-4-[(4-benzyloxy-2-methylphenyl)-methyl]-1,2-dihydro-5-isopropyl-3H-pyrazol-3-one.

$^1$H-NMR (CDCl$_3$) δ (ppm): 1.02 (3H, d, J=6.9 Hz), 1.05-1.15 (30H, m), 1.18 (9H, s), 2.29 (3H, s), 2.5-2.65 (4H, m), 3.5-3.65 (3H, m), 3.87 (1H, dd, J=12.3 Hz, 5.8 Hz), 4.03 (1H, dd, J=12.3 Hz, 1.5 Hz), 4.95-5.1 (3H, m), 5.2-5.3 (1H, m), 5.3-5.4 (2H, m), 6.64 (1H, dd, J=8.5 Hz, 2.4 Hz), 6.8 (1H, d, J=2.4 Hz), 6.85 (1H, d, J=8.5 Hz), 7.25-7.4 (3H, m), 7.4-7.45 (2H, m)

Example 3

4-Benzyl-5-isopropyl-3-(2,3,4,6-tetra-O-pivaloyl-β-D-glucopyranosyloxy)-1H-pyrazole To a solution of 1-acetyl-4-benzyl-5-isopropyl-3-(2,3,4,6-tetra-O-pivaloyl-β-D-glucopyranosyloxy)-1H-pyrazole (2.68 g) in methanol (27 mL) was added sodium bicarbonate (0.596 g) under stirring at room temperature. The reaction mixture was stirred at room temperature for 17 hours. After confirming the completion of the reaction, water was added to the reaction mixture in order to precipitate the crystals. The crystals were collected by filtration, and the obtained crystals were washed with water and dried under reduced pressure to give 4-benzyl-5-isopropyl-3-(2,3,4,6-tetra-O-pivaloyl-β-D-glucopyranosyloxy)-1H-pyrazole (2.45 g).

$^1$H-NMR (CDCl$_3$) δ (ppm): 1.06 (9H, s), 1.10-1.17 (33H, m), 2.82-2.90 (1H, m), 3.65 (2H, s), 3.84-3.87 (1H, m), 4.10-4.21 (2H, m), 5.23 (1H, t, J=9.5 Hz), 5.26-5.30 (1H, m), 5.38 (1H, t, J=9.5 Hz), 5.69 (1H, d, J=8.5 Hz), 7.11-7.21 (5H, m), 8.74 (1H, br-s)

Example 4

4-[(4-Benzyloxy-2-methylphenyl)methyl]-5-isopropyl-3-(2,3,4,6-tetra-O-pivaloyl-β-D-glucopyranosyloxy)-1H-pyrazole 4-[(4-Benzyloxy-2-methylphenyl)methyl]-5-isopropyl-3-(2,3,4,6-tetra-O-pivaloyl-β-D-glucopyranosyloxy)-1H-pyrazole was prepared in a similar manner described in (Example 3) using 1-acetyl-4-[(4-benzyloxy-2-methylphenyl)methyl]-5-isopropyl-3-(2,3,4,6-tetra-O-pivaloyl-β-D-glucopyranosyl-oxy)-1H-pyrazole.

$^1$H-NMR (CDCl$_3$) δ (ppm): 1.04 (9H, s), 1.05-1.2 (33H, m), 2.27 (3H, s), 2.7-2.85 (1H, m), 3.45-3.6 (2H, m), 3.8-3.9 (1H, m), 4.11 (1H, dd, J=12.6 Hz, 4.8 Hz), 4.17 (1H, dd, J=12.6 Hz, 1.8 Hz), 5.0 (2H, s), 5.15-5.3 (2H, m), 5.37 (1H, t, J=9.5 Hz), 5.65 (1H, d, J=7.8 Hz), 6.64 (1H, dd, J=8.4 Hz, 2.8 Hz), 6.77 (1H, d, J=2.8 Hz), 6.83 (1H, d, J=8.4 Hz), 7.25-7.45 (5H, m)

Example 5

4-Benzyl-5-isopropyl-1-propionyl-3-(2,3,4,6-tetra-O-pivaloyl-β-D-glucopyranosyloxy)-1H-pyrazole To a solution of 4-benzyl-1,2-dihydro-5-isopropyl-1-propionyl-3H-pyrazol-3-one (1.25 g) in acetonitrile (25 mL) were added potassium carbonate (0.951 g) and 2,3,4,6-tetra-O-pivaloyl-β-D-glucopyranosyl bromide (2.79 g) under stirring at room temperature. In addition, the mixture was heated to 50° C. and stirred for 3 hours. After the completion of the reaction, the insoluble materials were removed by filtration, and the filtrate was concentrated under reduced pressure. The residue was purified by column chromatography on silica gel (eluent: n-hexane/ethyl acetate=20/1) to give 4-benzyl-5-isopropyl-1-propionyl-3-(2,3,4,6-tetra-O-pivaloyl-β-D-glucopyranosyl-oxy)-1H-pyrazole (3.00 g).

$^1$H-NMR (CDCl$_3$) δ (ppm): 1.02-1.04 (6H, m), 1.05 (9H, s), 1.12 (9H, s), 1.13 (9H, s), 1.20 (9H, s), 1.20-1.21 (3H, m), 2.51-2.59 (1H, m), 2.95-3.12 (2H, m), 3.65-3.76 (3H, m), 3.92-3.95 (1H, m), 4.08-4.11 (1H, m), 5.13 (1H, t, J=9.5 Hz), 5.27-5.31 (1H, m), 5.42 (1H, t, J=9.5 Hz), 5.50 (1H, d, J=8.0 Hz), 7.15-7.33 (5H, m)

Example 6

4-Benzyl-5-isopropyl-3-(2,3,4,6-tetra-O-pivaloyl-β-D-glucopyranosyloxy)-1H-pyrazole To a solution of 4-benzyl-5-isopropyl-1-propionyl-3-(2,3,4,6-tetra-O-pivaloyl-β-D-glucopyranosyloxy)-1H-pyrazole (3.00 g) in methanol (30 mL) was added sodium bicarbonate (0.654 g) under stirring at room temperature. The reaction mixture was stirred at room temperature for 17 hours. After confirming the completion of the reaction, water was added to the mixture to precipitate the crystals. The crystals were collected by filtration. The obtained crystals were washed with water and dried under reduced pressure to give 4-benzyl-5-isopropyl-3-(2,3,4,6-tetra-O-pivaloyl-β-D-glucopyranosyl-oxy)-1H-pyrazole (2.67 g).

Example 7

1-Acetyl-4-benzyl-5-methyl-3-(2,3,4,6-tetra-O-pivaloyl-β-D-glucopyranosyloxy)-1H-pyrazole To a suspension of 1-acetyl-4-benzyl-1,2-dihydro-5-methyl-3H-pyrazol-3-one (0.75 g) in acetonitrile (5 mL) and tetrahydrofuran (3 mL) was added potassium carbonate (0.675 g) under stirring at room temperature. After the mixture was stirred at 50° C. for 1 hour, 1-bromo-2,3,4,6-tetra-O-pivaloyl-α-D-glucopyranosyl bromide (2.27 g) was added to the mixture. The mixture was stirred at 50° C. for 6 hours. After the reaction completed, the insoluble materials were removed by filtration, and the filtrate was concentrated under reduced pressure. The residue was purified by column chromatography on silica gel (eluent: ethyl acetate/n-hexane=1/10 to 1/5) to give 1-acetyl-4-benzyl-5-methyl-3-(2,3,4,6-tetra-O-pivaloyl-β-D-glucopyranosyloxy)-1H-pyrazole (1.88 g).

$^1$H-NMR (CDCl$_3$) δ ppm: 1.00 (9H, s), 1.13 (9H, s), 1.16 (9H, s), 1.18 (9H, s), 2.47 (3H, s), 2.54 (3H, s), 3.60 (2H, s), 3.89-3.92 (1H, m), 4.12-4.19 (2H, m), 5.23 (1H, t, J=9.6 Hz), 5.29-5.32 (1H, m), 5.43 (1H, t, J=9.5 Hz), 5.84 (1H, d, J=8.2 Hz), 7.13-7.22 (3H, m), 7.22-7.26 (2H, m)

Example 8

1-Acetyl-4-[(4-isopropoxyphenyl)methyl]-5-methyl-3-(2,3,4,6-tetra-O-pivaloyl-β-D-glucopyranosyloxy)-1H-pyrazole To a suspension of 1-acetyl-1,2-dihydro-4-[(4-isopropoxyphenyl)methyl]-5-methyl-3H-pyrazol-3-one (1.00 g) in acetonitrile (5 mL) and tetrahydrofuran (3 mL) was added potassium carbonate (0.719 g) under stirring at room temperature. After stirring the mixture at 50° C. for 1 hour, 2,3,4,6-tetra-O-pivaloyl-α-D-glucopyranosyl bromide (2.35 g) was added to the mixture. The mixture was stirred at 50° C. for 12 hours. After the reaction completed, the insoluble materials were removed by filtration, and the filtrate was concentrated under reduced pressure. 2-Propanol was added to the residue, and the mixture was re-concentrated under reduced pressure. The residue was recrystallized in the mixed solvent of water and methanol, the obtained crystals were dried under reduced pressure to give 1-acetyl-4-[(4-isopropoxyphenyl)methyl]-5-methyl-3-(2,3,4,6-tetra-O-pivaloyl-β-D-glucopyranosyloxy)-1H-pyrazole (2.19 g).

$^1$H-NMR (CDCl$_3$) δ (ppm): 1.01 (9H, s), 1.13 (9H, s), 1.16 (9H, s), 1.18 (9H, s), 1.28-1.30 (6H, m), 2.47 (3H, s), 2.54 (3H, s), 3.53 (2H, s), 3.89-3.92 (1H, m), 4.12-4.20 (2H, m), 4.46-4.49 (1H, m), 5.23 (1H, t, J=9.7 Hz), 5.29-5.32 (1H, m), 5.43 (1H, t, J=9.4 Hz), 5.84 (1H, d, J=8.2 Hz), 6.75-6.77 (2H, m), 7.01-7.03 (2H, m)

Example 9

1-Acetyl-4-[(3-fluoro-4-methylphenyl)methyl]-5-methyl-3-(2,3,4,6-tetra-O-pivaloyl-β-D-glucopyranosyloxy)-1H-pyrazole To a suspension of 1-acetyl-4-[(3-fluoro-4-methyl-phenyl)methyl]-1,2-dihydro-5-methyl-3H-pyrazol-3-one (0.32 g) in acetonitrile (3 mL) and tetrahydrofuran (1 mL) was added potassium carbonate (0.253 g) under stirring at room temperature. After stirring the mixture at 50° C. for 1 hour, 2,3,4,6-tetra-O-pivaloyl-α-D-glucopyranosyl bromide (0.849 g) was added to the mixture. The mixture was stirred at 50° C. for 2 hours. After the reaction completed, the insoluble materials were removed by filtration, and the filtrate was concentrated under reduced pressure. The residue was purified by column chromatography on silica gel (eluent: ethyl acetate/n-hexane=1/10 to 1/5) to give 1-acetyl-4-[(3-fluoro-4-methyl-phenyl)methyl]-5-methyl-3-(2,3,4,6-tetra-O-pivaloyl-β-D-glucopyranosyloxy)-1H-pyrazole (0.884 g).

¹H-NMR (CDCl₃) δ (ppm): 1.00 (9H, s), 1.13 (9H, s), 1.16 (9H, s), 1.17 (9H, s), 2.20 (3H, s), 2.46 (3H, s), 2.55 (3H, s), 3.56 (2H, s), 3.88-3.91 (1H, m), 4.11-4.19 (2H, m), 5.22 (1H, t, J=9.6 Hz), 5.27-5.30 (1H, m), 5.43 (1H, t, J=9.5 Hz), 5.83 (1H, d, J=8.2 Hz), 6.74 (1H, d, J=11 Hz), 6.82 (1H, t, J=1.6 Hz), 7.03 (1H, t, J=7.9 Hz)

Example 10

4-Benzyl-5-methyl-3-(2,3,4,6-tetra-o-pivaloyl-β-D-glucopyranosyloxy)-1H-pyrazole To a solution of 1-acetyl-4-benzyl-5-methyl-3-(2,3,4,6-tetra-O-pivaloyl-β-D-glucopyranosyloxy)-1H-pyrazole (1.00 g) in methanol (10 mL) was added potassium bicarbonate (0.058 g) under stirring at room temperature. The reaction mixture was stirred at room temperature for 16 hours. After the precipitation of the crystals by the addition of a solution of glacial acetic acid (0.034 g) in water (20 mL) at room temperature, the mixture was stirred for 2 hours. After the suspension was stirred under ice-cooling for 1 hour, the crystals were collected by filtration. The obtained crystals were washed with a mixed solution of 2-propanol and n-heptane, and dried under reduced pressure to give 4-benzyl-5-methyl-3-(2,3,4,6-tetra-O-pivaloyl-β-D-glucopyranosyloxy)-1H-pyrazole (0.90 g).

¹H-NMR (CDCl₃) δ (ppm): 1.05 (9H, s), 1.12 (9H, s), 1.15 (9H, s), 1.18 (9H, s), 2.06 (3H, s), 3.62 (2H, s), 3.84-3.88 (1H, m), 4.10-4.21 (2H, m), 5.22-5.31 (2H, m), 5.38 (1H, t, J=9.3 Hz), 5.67 (1H, d, J=8.0 Hz), 7.11-7.15 (3H, m), 7.21-7.23 (2H, m)

Example 11

4-[(4-Isopropoxyphenyl)methyl]-5-methyl-3-(2,3,4,6-tetra-O-pivaloyl-β-D-glucopyranosyloxy)-1H-pyrazole To a suspension of 1-acetyl-4-[(4-isopropoxyphenyl)-methyl]-5-methyl-3-(2,3,4,6-tetra-O-pivaloyl-β-D-glucopyranosyloxy)-1H-pyrazole (1.00 g) in methanol (10 mL) was added potassium bicarbonate (0.038 g) under stirring at room temperature. The suspension turned into a solution by heating to reflux, and the mixture was stirred for further 2 hours. After confirming the completion of the reaction, a solution of glacial acetic acid (0.022 g) in water (10 mL) was added to the mixture at 60° C. to precipitate the crystals. The suspension was cooled to room temperature, and stirred under ice-cooling for 1 hour. The crystals were collected by filtration, and the obtained crystals were washed with a mixed solution of 2-propanol and n-heptane, and dried under reduced pressure to give 4-[(4-isopropoxyphenyl)methyl]-5-methyl-3-(2,3,4,6-tetra-O-pivaloyl-β-D-glucopyranosyloxy)-1H-pyrazole (0.890 g).

¹H-NMR (CDCl₃) δ (ppm): 1.05 (9H, s), 1.12 (9H, s), 1.15 (9H, s), 1.18 (9H, s), 1.28-1.30 (6H, m), 2.06 (3H, s), 3.54 (2H, s), 3.83-3.87 (1H, m), 4.11-4.20 (2H, m), 4.44-4.49 (1H, m), 5.22-5.31 (2H, m), 5.38 (1H, t, J=9.4 Hz), 5.67 (1H, d, J=8.2 Hz), 6.73-6.76 (2H, m), 7.02-7.04 (2H, m), 8.69 (1H, br-s)

Example 12

4-[(3-Fluoro-4-methylphenyl)methyl]-5-methyl-3-(2,3,4,6-tetra-O-pivaloyl-β-D-glucopyranosyloxy)-1H-pyrazole To a solution of 1-acetyl-4-[(3-fluoro-4-methylphenyl)-methyl]-5-methyl-3-(2,3,4,6-tetra-O-pivaloyl-β-D-glucopyranosyloxy)-1H-pyrazole (0.75 g) in methanol (5 mL) was added potassium bicarbonate (0.030 g) under stirring at room temperature. The mixture was stirred at 50° C. for 3 hours. To the mixture was added glacial acetic acid (0.022 g) at 60° C., and the resulting mixture was concentrated under reduced pressure. The residue was purified by column chromatography on silica gel (eluent: ethyl acetate/n-hexane=1/5) to give 4-[(3-fluoro-4-methylphenyl)methyl]-5-methyl-3-(2,3,4,6-tetra-O-pivaloyl-β-D-glucopyranosyloxy)-1H-pyrazole (0.610 g).

¹H-NMR (CDCl₃) δ (ppm): 1.05 (9H, s), 1.12 (9H, s), 1.15 (9H, s), 1.18 (9H, s), 2.07 (3H, s), 2.20 (3H, s), 3.57 (2H, s), 3.85-3.88 (1H, m), 4.12-4.20 (2H, m), 5.23-5.30 (2H, m), 5.38 (1H, t, J=9.4 Hz), 5.60 (1H, d, J=8.1 Hz), 6.74-6.77 (1H, m), 6.81-6.83 (1H, m), 7.02 (1H, t, J=7.9 Hz)

Example 13

1-Benzyloxycarbonyl-4-benzyl-5-isopropyl-3-(2,3,4,6-tetra-O-pivaloyl-β-D-glucopyranosyloxy)-1H-pyrazole To a solution of 1-benzyloxycarbonyl-4-benzyl-5-isopropyl-1,2-dihydro-3H-pyrazol-3-one (0.16 g) in acetonitrile (5 mL) were added potassium carbonate (0.0757 g) and 2,3,4,6-tetra-O-pivaloyl-α-D-glucopyranosyl bromide (0.278 g) successively under stirring at room temperature. In addition, the mixture was stirred at 50° C. for 4 hours. The reaction mixture was poured into water, and the resulting mixture was extracted with diethyl ether. The organic layer was washed with brine and dried over anhydrous magnesium sulfate. The insoluble materials were removed by filtration, and the filtrate was concentrated under reduced pressure. The residue was purified by column chromatography on silica gel (eluent: ethyl acetate/n-hexane=1/6) to give 1-benzyloxycarbonyl-4-benzyl-5-isopropyl-3-(2,3,4,6-tetra-O-pivaloyl-β-D-glucopyranosyl-oxy)-1H-pyrazole (0.228 g).

¹H-NMR (CDCl₃) δ (ppm): 1.05-1.20 (42H, m), 2.55-2.70 (1H, m), 3.40-3.50 (1H, m), 3.70 (1H, d, J=16.7 Hz), 3.74 (1H, d, J=16.7 Hz), 3.87 (1H, dd, J=12.3, 6.1 Hz), 3.97 (1H, dd, J=12.3, 1.7 Hz), 4.85-4.95 (1H, m), 5.11-5.17 (2H, m), 5.22-5.25 (1H, m), 5.41 (1H, d, J=12.1 Hz), 5.45 (1H, d, J=12.1 Hz), 7.05-7.15 (2H, m), 7.15-7.30 (3H, m), 7.35-7.55 (5H, m)

Example 14

4-Benzyl-5-isopropyl-3-(2,3,4,6-tetra-O-pivaloyl-β-D-glucopyranosyloxy)-1H-pyrazole To a solution of 1-benzyloxycarbonyl-4-benzyl-5-isopropyl-3-(2,3,4,6-tetra-O-pivaloyl-β-D-glucopyranosyl-oxy)-1H-pyrazole (0.228 g) in methanol (5 mL) was added 10% palladium on carbon (50% wet: 0.40 g). In addition, the mixture was stirred under a hydrogen atmosphere at room temperature for 13 hours. The insoluble materials were removed by filtration through Celite®, and the filtrate was concentrated under reduced pressure to give 4-benzyl-5-isopropyl-3-(2,3,4,6-tetra-O-pivaloyl-β-D-glucopyranosyloxy)-1H-pyrazole (0.186 g).

Example 15

4-Benzyl-1-ethoxycarbonyl-5-isopropyl-3-(2,3,4,6-tetra-O-pivaloyl-β-D-glucopyranosyloxy)-1H-pyrazole To a solution of 4-benzyl-1-ethoxycarbonyl-1,2-dihydro-5-isopropyl-3H-pyrazol-3-one (0.100 g) in acetonitrile (3 mL) were added potassium carbonate (0.0575 g) and 2,3,4,6-tetra-O-pivaloyl-α-D-glucopyranosyl bromide (0.211 g) successively under stirring at room temperature. In addition, the mixture was stirred at 50° C. for 2.5 hours. The mixture was poured into water, and the resulting mixture was extracted with diethyl ether. The organic layer was washed with brine and dried over anhydrous magnesium sulfate. The insoluble materials were removed by filtration, and the filtrate was concentrated under reduced pressure. The residue was purified by column chromatography on silica gel (eluent: ethyl acetate/n-hexane=1/8 to 1/5 to 1/4) to give 4-benzyl-1-ethoxycarbonyl-5-isopropyl-3-(2,3,4,6-tetra-O-pivaloyl-β-D-glucopyranosyloxy)-1H-pyrazole (0.15 g).

$^1$H-NMR (CDCl$_3$) δ (ppm): 1.05-1.10 (15H, m), 1.12 (9H, s), 1.13 (9H, s), 1.18 (9H, s), 1.44 (1H, t, J=7.1 Hz), 2.62-2.68 (1H, m), 3.55-3.65 (1H, m), 3.75 (2H, s), 3.97 (1H, dd, J=12.4, 5.3 Hz), 4.05 (1H, dd, J=12.4, 1.8 Hz), 4.40-4.55 (1H, m), 5.11-5.15 (1H, m), 5.25-5.37 (3H, m), 7.12-7.26 (5H, m)

Example 16

4-Benzyl-5-isopropyl-3-(2,3,4,6-tetra-O-pivaloyl-β-D-glucopyranosyloxy)-1H-pyrazole To a solution of 4-benzyl-1-ethoxycarbonyl-5-isopropyl-3-(2,3,4,6-tetra-O-pivaloyl-β-D-glucopyranosyl-oxy)-1H-pyrazole (0.15 g) in methanol (3 mL) was added sodium bicarbonate (0.032 g) under stirring at room temperature. The mixture was stirred at room temperature for 12 hours. In addition, to the mixture was added potassium carbonate (0.053 g), and the mixture was stirred for 2 hours. The reaction mixture was poured into water to precipitate the solid. The solids were collected by filtration. The obtained solids were washed with water and dried under reduced pressure to give 4-benzyl-5-isopropyl-3-(2,3,4,6-tetra-O-pivaloyl-β-D-glucopyranosyloxy)-1H-pyrazole (0.098 g).

Example 17

4-Benzyl-1-formyl-5-isopropyl-3-(2,3,4,6-tetra-O-pivaloyl-β-D-glucopyranosyloxy)-1H-pyrazole To solution of 4-benzyl-1,2-dihydro-1-formyl-5-isopropyl-3H-pyrazol-3-one (1.07 g) in acetonitrile (20 mL) were added potassium carbonate (0.905 g) and 2,3,4,6-tetra-O-pivaloyl-β-D-glucopyranosyl bromide (2.65 g) under stirring at room temperature. In addition, the mixture was heated to 50° C. and stirred for 1 hour. After the reaction completed, the insoluble materials were removed by filtration, and the filtrate was concentrated under reduced pressure. The residue was purified by column chromatography on silica gel (eluent: n-hexane/ethyl acetate=10/1) to give 4-benzyl-1-formyl-5-isopropyl-3-(2,3,4,6-tetra-O-pivaloyl-β-D-glucopyranosyl-oxy)-1H-pyrazole (1.49 g).

$^1$H-NMR (CDCl$_3$) δ (ppm): 1.09-1.13 (33H, m), 1.16 (9H, s), 2.62-2.68 (1H, m), 3.59 (1H, br-s), 3.69-3.81 (2H, m), 3.95-3.98 (1H, m), 4.05-4.07 (1H, m), 5.11-5.32 (4H, m), 7.09-7.13 (2H, m), 7.20-7.29 (3H, m), 9.03 (1H, s)

Example 18

4-Benzyl-5-isopropyl-3-(2,3,4,6-tetra-O-pivaloyl-β-D-glucopyranosyloxy)-1H-pyrazole To a solution of 4-benzyl-1-formyl-5-isopropyl-3-(2,3,4,6-tetra-O-pivaloyl-β-D-glucopyranosyloxy)-1H-pyrazole (1.49 g) in methanol (15 mL) was added sodium bicarbonate (0.337 g) under stirring at room temperature. The reaction mixture was stirred at room temperature for 11 hours. After confirming the completion of the reaction, water was added to the mixture to precipitate the crystals. The crystals were collected by filtration, and the obtained crystals were washed with water and dried under reduced pressure to give 4-benzyl-5-isopropyl-3-(2,3,4,6-tetra-O-pivaloyl-β-D-glucopyranosyl-oxy)-1H-pyrazole (1.40 g).

INDUSTRIAL APPLICABILITY

According to a method for the preparation of the present invention, glucopyranosyloxypyrazole derivatives, for example, the glucopyranosyloxypyrazole derivative represented by the above general formula (A) or a pharmaceutically acceptable salt thereof, which are useful as agents for the prevention or treatment of a disease associated with hyperglycemia such as diabetes, diabetic complications, obesity or the like can be easily and efficiently prepared, the present invention is extremely useful as a method for preparing the pharmaceutical compounds represented by the above general formula (A).

The invention claimed is:
1. A method for preparing a glucopyranosyloxypyrazole derivative represented by the general formula:

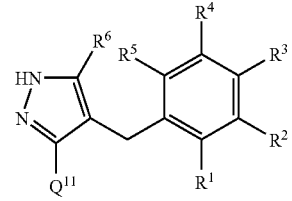

[Chem. 14]

wherein $Q^{11}$ is a group represented by the general formula:

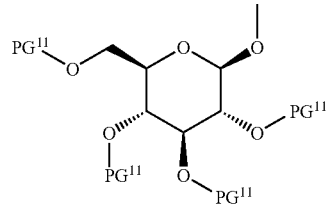

[Chem.13]

in which $PG^{11}$ is an arylcarbonyl group, a pivaloyl group or an arylmethyl group, and $R^1$, $R^2$, $R^3$, $R^4$ and $R^5$ may be the same or different, each of them is a hydrogen atom, a halogen atom, a $C_{1-6}$ alkyl group, a halo$C_{1-6}$ alkyl group, a $C_{3-6}$ cycloalkyl group, a $C_{3-6}$ cycloalkyloxy group, a $C_{3-6}$ cycloalkyl($C_{1-6}$ alkoxy)group, a $C_{1-6}$ alkoxy group, a $C_{1-6}$ alkylthio group, a halo$C_{1-6}$ alkoxy group, an aryl group, an aryloxy group, a heteroaryl group, an aryl($C_{1-6}$ alkyl) group, an aryl($C_{1-6}$ alkoxy) group, a $C_{2-6}$ alkenyl group, a $C_{2-6}$ alkynyl group, a hetero$C_{3-6}$ cycloalkyl group, a hetero$C_{3-6}$ cycloalkyloxy group, a hetero$C_{3-6}$ cycloalkyl($C_{1-6}$ alkyl)group, a $C_{1-6}$ alkoxy group substituted by an amino group which is mono-substituted by a $C_{1-6}$ alkyl group or a $C_{1-6}$ alkoxy group substituted by an amino group which is di-substituted by a $C_{1-6}$ alkyl group, and $R^6$ is a $C_{1-6}$ alkyl group, a halo$C_{1-6}$ alkyl group or a $C_{3-6}$ cycloalkyl group, which comprises allowing a benzylpyrazole derivative represented by the general formula:

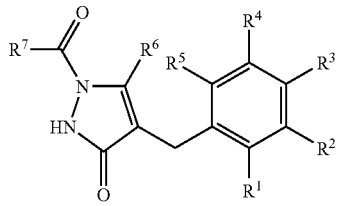
[Chem. 10]

wherein $R^1$, $R^2$, $R^3$, $R^4$, $R^5$ and $R^6$ have the same meanings as defined above, and $R^7$ is a hydrogen atom, a $C_{1-6}$ alkyl group, a $C_{1-6}$ alkoxy group or an arylmethyloxy group to react with a compound represented by the general formula:

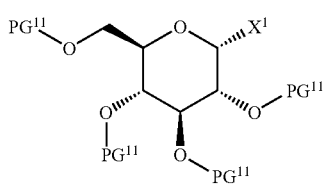
[Chem. 11]

in which $PG^{11}$ has the same meaning as defined above, and $X^1$ is a bromine atom or a chlorine atom in the presence of a base selected from the group consisting of potassium tert-butoxide, potassium carbonate, sodium carbonate and cesium carbonate to yield a glucopyranosyloxypyrazole derivative represented by the general formula:

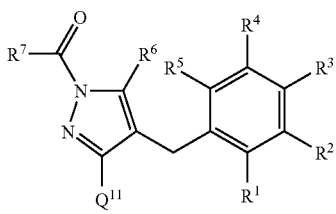
[Chem. 12]

wherein $R^1$, $R^2$, $R^3$, $R^4$, $R^5$, $R^6$ and $R^7$ have the same meanings as defined above, and subsequently removing $R^7$ CO— on the pyrazole ring.

\* \* \* \* \*